United States Patent [19]

Bryant et al.

[11] Patent Number: 5,407,947
[45] Date of Patent: Apr. 18, 1995

[54] METHODS FOR INHIBITING BONE LOSS USING PYROLIDINE AND PIPERIDINE SUBSTITUTED BENZOPYRANS

[75] Inventors: Henry U. Bryant; Timothy A. Grese, both of Indianapolis, Ind.

[73] Assignee: Eli Lilly and Company, Indianapolis, Ind.

[21] Appl. No.: 148,786
[22] Filed: Nov. 5, 1993
[51] Int. Cl.$^6$ .................. A61K 31/445; A61K 31/44; A61K 31/40
[52] U.S. Cl. .................................. 514/320; 514/337; 514/422
[58] Field of Search ....................... 514/422, 337, 320
[56] References Cited

U.S. PATENT DOCUMENTS 5,183,814  2/1993  Dukes .................................. 514/171

FOREIGN PATENT DOCUMENTS

0470310A1  2/1992  European Pat. Off.
PCT/CA92/-
00518  12/1992  WIPO

OTHER PUBLICATIONS

Sreenivasulu, S., et al., "studies on competition to estrogen binding sites in the immature rat uterus," *Indian J. Exp. Biol.*, 30(12), 1115–17, (Dec. 1992).
Sreenivasulu, S., et al., "Duration of antiestrogenecity of compound CdRI-85/287: a new orally active nonsteroidal antiimplantation agent," *Indian J. Exp. Biol.*, 30(11), 968–71, (Nov. 1992).
Sreenivasulu, S., et al., "CDRI-85/287, a novel antiestrogen and antiimplantation agent: biological profile and interaction with the estrogen receptors in immature rat uterus," *Contraception*, 45(1), 81–92, (Jan. 1992).
Dhar, J. D., et al., "Biological profile of 2-[4-(-2-N-piperidinoethoxy)phenyl]-3-phenyl (2H) benzo(B)pyran-a potent antiimplantation agent in rats," *Contraception*, 44(4), 461–72, (Oct. 1991).
Saeed, A., et al. "Structure–activity relationship of antiestrogens, studies on 2, 3-diaryl-1-benzopyrans" *J. Med. Chem.*, 33(12), 3210–16, (1990).
Sharma, A. P., et al., "Structure–activity relationship of antiestrogens, effect of the side chain and its position on activity of 2,3-diaryl-2H-1-benzopyrans" *J. Med. Chem.*, 33(12), 3216–22, (1990).
Sharma, A. P., et al., "Structure–activity relationship of antiestrogens. Phenolic analogs of 2,3-diaryl-2-H-1-benzopyrans," *J. Med. Chem.*, 33(12), 3222–9, (1990).
Dhar, J. D., et al., "Biological profile of 2-[4-(-2-N-piperidinoethoxy) phenyl]-3-phenyl (2H) benzo(b) pyran," *Contraception* 45(4), 397–398, (1990).
Verm et al., "Synthesis of 3-aryl-1-(4-methoxy phenyl)-2-[4-(2-substituted aminoethoxy) phenyl]-L-propen-1-ones and benzopyran derivative," *Indian J. of Chem.*, 32B, 239–243 (Feb. 1993).

*Primary Examiner*—Raymond Henley, III
*Assistant Examiner*—T. J. Craires
*Attorney, Agent, or Firm*—James J. Sales; Gerald V. Dahling

[57] ABSTRACT

A method of inhibiting bone loss comprising administering to an animal an effective amount of a compound having the formula

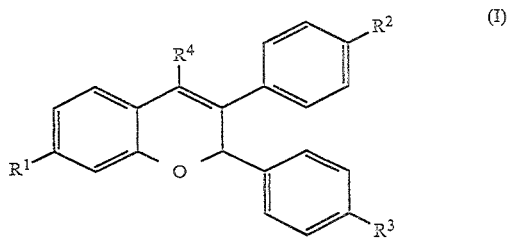

wherein:
R$^1$ and R$^2$ are, independently, —H, —OH, halo, —OC$_1$-C$_{17}$ alkyl, —OC$_3$-C$_6$ cycloalkyl, —O(CO)C$_1$-C$_{17}$ alkyl, —O(CO) aryl, —O(CO)O aryl, or —OSO$_2$-(n-butyl or n-pentyl);
R$^3$ is

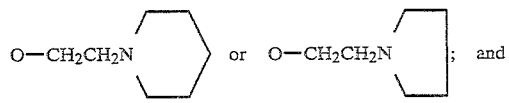

R$^4$ is —H, methyl, ethyl, propyl, ethenyl or ethynyl; or a pharmaceutically acceptable salt or solvate thereof.

19 Claims, No Drawings

METHODS FOR INHIBITING BONE LOSS USING PYROLIDINE AND PIPERIDINE SUBSTITUTED BENZOPYRANS

BACKGROUND OF THE INVENTION

The mechanism of bone loss is not completely understood, but bone loss disorders arise from an imbalance in the formation of new healthy bone and the resorption of old bone, skewed toward a net loss of bone tissue. This bone loss involves a decrease in both mineral content and protein matrix components of the bone. Ultimately, such bone loss leads to an increased fracture rate of, predominantly, femoral bones and bones in the forearm and vertebrae. These fractures, in turn, lead to an increase in general morbidity, a marked loss of stature and mobility, and, in many cases, an increase in mortality resulting from complications.

Bone loss occurs in a wide range of subjects, including post-menopausal women, patients who have undergone hysterectomy, patients who are undergoing or have undergone long-term administration of corticosteroids, patients suffering from Cushing's syndrome, and patients having gonadal dysgenesis. The need for bone repair or replacement also arises locally in the case of bone fracture, non-union, defect, prosthesis implantation, and the like. Further, such need also arises in cases of systemic bone diseases, as in osteoporosis, osteoarthritis, Paget's disease, osteomalacia, osteohalisteresis, multiple myeloma and other forms of cancer and the like.

SUMMARY OF THE INVENTION

This invention provides methods for inhibiting bone loss, comprising administering to an animal an amount that inhibits bone loss of a compound of formula (I):

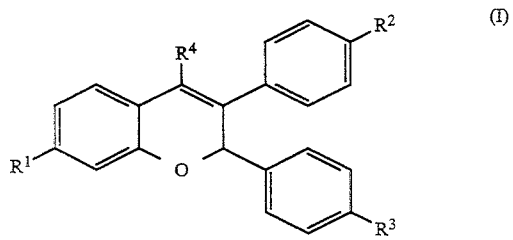

wherein:
$R^1$ and $R^2$ are, independently, —H, —OH, halo, —$OC_1$-$C_{17}$ alkyl, —$OC_3$-$C_6$ cycloalkyl, —O(-CO)$C_1$-$C_{17}$ alkyl, —O(CO) aryl, —O(CO)O aryl, or —$OSO_2$-(n-butyl or n-pentyl);
$R^3$ is

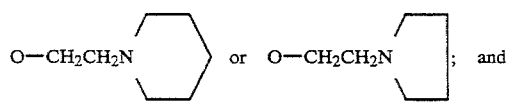

$R^4$ is —H, methyl, ethyl, propyl, ethenyl or ethynyl; or a pharmaceutically acceptable salt or solvate thereof.

DETAILED DESCRIPTION OF THE INVENTION

The general chemical terms used in the description of a compound of formula I have their usual meanings. For example, the term "alkyl" by itself or as part of another substituent means a straight or branched chain alkyl radical having the stated number of carbon atoms, such as methyl, ethyl, propyl and isopropyl, and higher homologs and isomers where indicated.

The term "cycloalkyl" means a cyclic alkyl radical having the stated number of carbon atoms. Examples of cycloalkyl groups are cyclopropyl, cyclopentyl and cyclohexyl.

The term "aryl" includes groups such as phenyl, naphthyl, thienyl or furyl, each of which may be unsubstituted or monosubstituted with a group selected from hydroxyl, halo, $C_1$-$C_3$ alkyl, or $C_1$-$C_3$ alkoxy.

The term "halo" means chloro, fluoro, bromo or iodo.

Specific examples of the compounds of formula I include the following:

Compound 1 2-[4-[2-(1-piperidino)ethoxy]phenyl]-3-(4-hydroxyphenyl)-7-hydroxy-2H-1-benzopyran Compound 2 2-[4-[2-(1-piperidino)ethoxy]phenyl]-3-(4-hydroxyphenyl)-2H-1-benzopyran Compound 3 2-[4-[2-(1-piperidino)ethoxy]phenyl]-3-phenyl-7-methoxy-2H-1-benzopyran Compound 4 2-[4-[2-(1-pyrrolidino)ethoxy]phenyl]-3-(4-hydroxyphenyl)-7-hydroxy-2H-1-benzopyran Compound 5 2-[4-[2-(1-piperidino)ethoxy]phenyl]-3-(4hydroxypheny)-4-methyl-7-hydroxy-2H-1-benzopyran The current invention concerns the discovery that the compounds of formula I are useful for inhibiting bone loss. The methods of treatment provided by this invention can be practiced by administering to an animal an amount that inhibits bone loss of a compound of formula I, or a pharmaceutically acceptable salt or solvate thereof. The methods include both medical therapeutic and/or prophylactic treatment, as appropriate. Generally, the formula I compound is formulated with common excipients, diluents or carriers, and put into capsules or compressed into tablets, or formulated as elixirs or solutions for convenient oral administration, or administered by the intramuscular or intravenous routes. The compounds may also be administered transdermally.

The methods of this invention also include the administration of a compound of formula I together with estrogen, either independently or in combination. The term estrogen as used herein refers to any compound which approximates the spectrum of activities of the naturally acting molecule which is commonly believed to be 17β-estradiol. Examples of such compounds include estriol, estrone, ethynyl estradiol, Premarin (a commercial preparation of conjugated estrogens isolated from natural sources—Ayerst), and the like.

All of the compounds used in the methods of the current invention can be made according to established or analogous procedures, such as those detailed in European Patent Application No. 0 470 310 A1 and PCT Application WO 93/10741. Modifications to these methods may be necessary to accommodate reactive functionalities of particular substituents. Such modifications would be either apparent to, or readily ascertained by, those skilled in the art.

Thus, the compounds of formula I in which $R^4$ is H can be manufactured, for example, by reacting a compound of formula II:

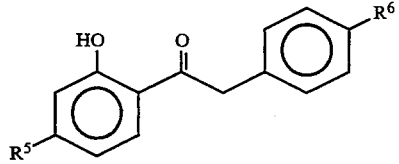

in which $R^5$ and $R^6$ are $R^1$ and $R^2$, respectively, or a protected hydroxyl group, with 4-hydroxybenzaldehyde to produce a compound of formula III:

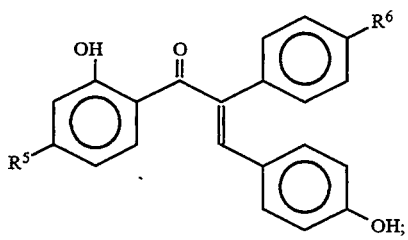

2) forming a compound of formula IV:

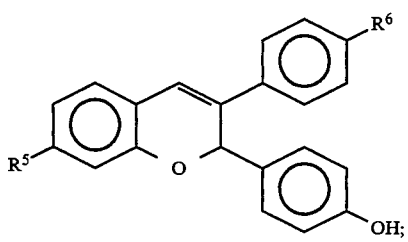

3) reacting this compound with a compound of formula V:

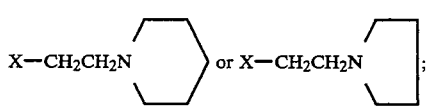

which X is a halide, to form a compound of formula VI:

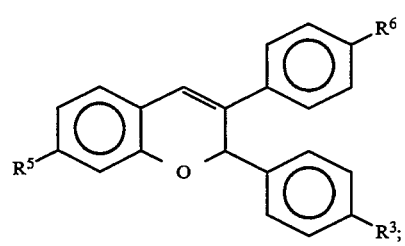

and, if necessary, 4) deprotecting and acylating or alkylating $R^5$ and $R^6$

Alternatively, the compounds of formula I in which $R^4$ is not H can be manufactured, for example, by reacting a compound of formula II in which $R^5$ and $R^6$ are $R^1$ and $R^2$, respectively, or a protected hydroxyl group, with 4-hydroxybenzaldehyde to produce a compound of formula VIII:

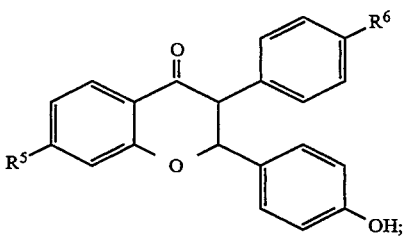

2) reacting this compound with a compound of formula V in which X is a halide to form a compound of formula X:

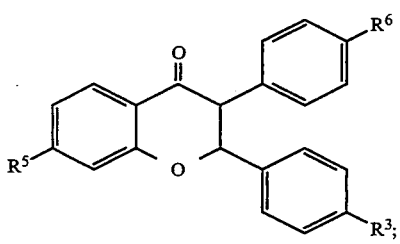

3) reacting this compound with a Grignard reagent of formula $R_4MgX$ in which X is a halide to form a compound of formula XI:

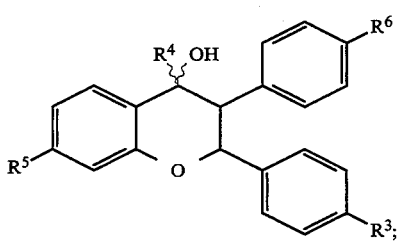

4) dehydrating compound XI to form a compound of formula XII:

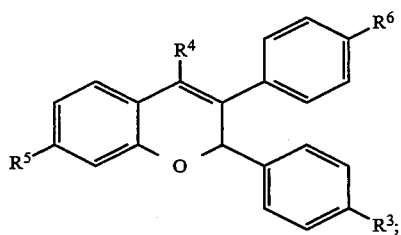

and, if necessary, 5) deprotecting and acylating or alkylating $R^5$ and $R^6$.

When producing the formula I compounds wherein $R^1$ is H, preferably in the above processes $R^5$ is H and $R^6$ is a protected hydroxy group.

When the processes are used to produce a formula I compound in which $R^1$ and $R^2$ are each alkoxy or carboxy, then $R^5$ and $R^6$ may be $R^1$ and $R^2$, respectively, or may each be in the form of a protected hydroxy group. If $R^1$ or $R^2$ is a hydroxy group, then $R^5$ or $R^6$, respectively, in the above process is preferably in the form of a protected hydroxy Group. If $R^5$ or $R^6$ is a protected group, then preferably the protecting group is 3,4-dihydropyran. The 3,4-hydropyran may be reacted with a compound of formula IX:

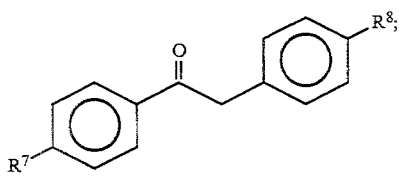

where one of $R^7$ and $R^8$ is a hydroxy group and the other is hydrogen or a hydroxy group or an alkoxy or carboxy group, to form a tetrahydropyranyl ether. Preferably the reaction is carried out in the presence of a sulphonic acid, such as para-toluene sulphonic acid or the like in an ether solvent, such as dioxan or the like. The reaction may be effected for a period of up to 4 hours; and the crude reaction product, after stipulated processing, may be purified, e.g., by crystallization from a petroleum solvent such as hexane or by rapid chromatography over silica gel.

The reaction of the compound of formula II with the 4-hydroxybenzaldehyde may be effected in the presence of a cyclic or open chain secondary and/or tertiary amino base such as piperidine or triethyl amine, and an aromatic hydrocarbon solvent such as benzene or the like. The solvent may be added at periodic intervals to replenish its loss during the reaction. This reaction may be effected for a period of about 30 hours. Thereafter, the reaction mixture may be cooled and washed with water, the organic layer separated, dried over $Na_2SO_4$ and concentrated. The solidified material may be filtered off, washed with a halogenated solvent such as chloroform, methylene dichloride or the like to give a compound of formula III. Generally, compound III will be produced as a mixture with a compound of formula VIII:

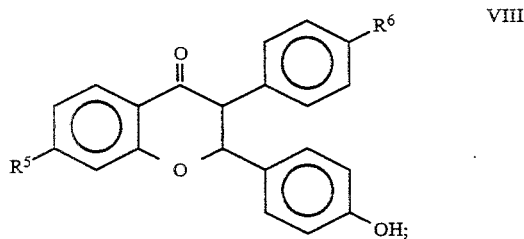

For example, the product mixture may contain a ratio of compound VIII to compound III of 1.0:1.5. The filtrate containing compounds III and VIII may be concentrated, chromatographed and eluted with an eluate of increasing polarity, such as ethyl acetate in hexane or the like, thereby separating out the compound of formula III.

The compound of the formula III may be converted to a compound of formula IV by reduction, for example by treating with a hydride such as sodium borohydride or the like in an alcoholic solvent such as ethyl alcohol or the like. Cyclodehydration may also be carried out; typically, work-up of the product, e.g., thermal work-up, may cause cyclodehydration. The hydride may be added in different proportions, at intervals of 10 to 15 minutes, at room temperature under stirring. The reaction may be continued a period of up to 12 to 15 hours. The reaction product, after concentration, pH adjustment and extraction with a polar solvent such as ethyl acetate, is purified by chromatography, e.g., flash chromatography over silica gel to yield a compound of formula IV.

The compound of formula IV can be treated with an appropriate heterocyclic alkyl halide, e.g., a piperidino- or pyrrolidinoalkyl halide, preferably in the presence of a basic catalyst such as potassium carbonate and a suitable ketonic solvent such as acetone or the like. This reaction may be followed by purification by chromatography, e.g., on alumina using hexane or a mixture thereof with a polar solvent to yield a compound of formula VI.

If $R^5$ and $R^6$ are not protected hydroxy groups, then the compound produced is a compound of formula I. If $R^5$ or $R^6$ is a protected hydroxy group, then the protecting group(s) may be removed by known methods, e.g., by use of an acid such as hydrochloric acid in an alcoholic solvent such as ethanol. The deprotected hydroxy group(s) may, if desired, be alkylated or acylated by known methods to give other compounds of formula I.

Alternatively, the compound of formula III can be converted to the compound of formula VIII by heating with sodium acetate in methanol.

The compound of formula VIII can be treated with an appropriate heterocyclic alkyl halide, e.g., a piperidino- or pyrrolidinoalkyl halide preferably in the presence of a basic catalyst such as potassium carbonate and a suitable ketonic solvent such as acetone or the like. This reaction may be followed by purification by chromatography, e.g., on silica gel using a mixture of hexane and a polar solvent containing a small amount of triethylamine or ammonium hydroxide, to yield a compound of formula X.

The compound of formula X can be treated with an appropriate Grignard reagent, e.g., methylmagnesium bromide or ethylmagnesium bromide, in diethyl ether or a tetrahydrofuran at 0° C. This reaction may be followed by purification by chromatography, e.g., on silica gel using a polar solvent such as ethyl acetate or acetone or a mixture thereof, to yield a compound of formula XI.

The compound of formula XI can be dehydrated by treating with acetic acid and water at 100° C. for 10 min. This reaction may be followed by purification by chromatography, e.g., on silica gel using a polar solvent such as ethyl acetate or acetone or a mixture thereof, to give a compound of formula XII.

when $R^5$ and $R^6$ are not protected hydroxy groups, then the compound produced is a compound of formula I. If $R^5$ and $R^6$ are hydroxy group(s) protected as the tetrahydropyranyl ether(s) they are also deprotected in this reaction to yield a compound of formula I in which $R^1$ and $R^2$ are hydroxy. The deprotected hydroxy group(s) may, if desired, by alkylated or acylated by known methods to give other compound of formula I.

The unprotected starting compound of formula II)′:

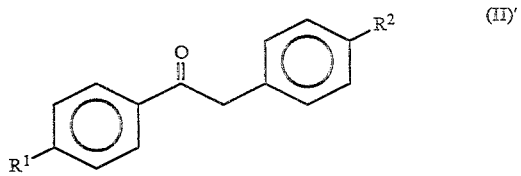

where $R^1$ and $R^2$ are as defined supra can be prepared by methods known in the art. For example, when $R^1$ is H and $R^2$ is OH, it can be prepared by condensation of phenol with 4-methoxy-phenylacetyl chloride (in turn prepared from 4-methoxy-phenylacetic acid) to afford an ester which on typical Fries rearrangement in the presence of anhydrous aluminum chloride yields a mixture which can be resolved chromatographically to afford the desired starting material that can be characterized by its physical and spectral data.

When $R^1$ is, e.g., methoxy and $R^2$ is as defined supra, the starting compound II' may be prepared by Friedel-Crafts acylation of a corresponding phenol, such as 3-methoxyphenol or the like, with a suitable substituted or unsubstituted phenylacetyl chloride, using a catalyst, such as anhydrous aluminum chloride. The resultant product may be purified by steam distillation and/or column chromatography.

In turn, when $R^1$ and $R^2$ are both OH, the starting compound can be prepared by Friedel-Crafts acylation of resorcinol with 4-methoxyphenyl acetyl chloride. This reaction affords a mixture of trihydroxydeoxybenzoin and methoxy dihydroxydeoxybenzoin. The latter compound may be converted into the desired trihydroxy compound by heating it with anhydrous pyridine hydrochloride.

The formula I compounds can form pharmaceutically acceptable acid and base addition salts with a variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methane-sulfonate, naphthalene-1-sulfonate, naphthalene-2-sulfonate, p-toluenesulfonate, xylenesulfonate, tartrate, and the like.

In addition, some of the formula I compounds may form solvates with water or organic solvents such as ethanol. These solvates are also contemplated for use in the methods of this invention.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the formula I compounds, either alone or in combination with estrogen, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The formula I compounds, either alone or in combination with estrogen, can also be formulated as elixirs or solutions for convenient oral administration or as solutions appropriate for parenteral administration, for instance by intramuscular, subcutaneous or intravenous routes. Additionally, the compounds, either alone or in combination with estrogen, can be formulated as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit bone loss according to this invention will depend upon the severity of the condition, the route of administration, and related factors. In humans, generally accepted and effective daily doses will be from about 0.1 to about 1000 mg, and more typically from about 50 to about 600 mg. Such dosages will be administered to the patient from once to about three times each day, or more often as needed to inhibit bone loss effectively.

If estrogen is also administered, generally accepted and effective daily doses of estrogen will be from about 0.01 to about 4.0 mg, and more typically from about 0.1 to about 2.0 mg. These doses are also administered to the patient from once to about three times a day, or more often as needed.

A preferred formula I compound of this invention is the compound wherein $R^1$ is H or OH;

$R^2$ is OH;

$R^3$ is

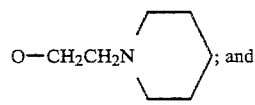; and $R^4$ is H or methyl.

It is usually preferable to administer the formula I compound in the form of an acid addition salt, as is customary in the administration of pharmaceuticals bearing a basic group, such as the piperidino ring. It is also advantageous to administer the compound orally.

A particularly important group of patients are aging humans (e.g., post-menopausal females).

For the purposes of this invention, the following are typical oral dosage forms. In these examples, "Active ingredient" means a compound of formula 1.

Capsules

Formulation 1:

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Tablets The components in Formulation I can be blended and compressed to form tablets.

Alternatively, tablets each containing 0.1–1000 mg of active ingredient are made up as follows:
Formulation 2:

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions

Suspensions each containing 0.1–1000 mg of medicament per 5 mL dose are made as follows:
Formulation 3:

| Ingredient | Quantity (amount/5 mL) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water | qs to 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The following nonlimiting test examples illustrate the methods of this invention.

Test Procedures

Six month old, female Sprague Dawley rats (weight range of 275 to 350 g; Harlan Sprague Dawley, Indianapolis, Ind.) are used in these studies. Ovariectomies (or a sham surgical procedure for controls) are performed by the vendor. The animals are shipped the day following surgery and housed in hanging wire cages. Room temperature is maintained at 22.2°±1.7° C. with a minimum relative humidity of 40%. The photoperiod in the room is 12 hr light and 12 hr dark, with light onset at 0600 hr. The animals ad lib access to food (Teklad diet, TD 89222, 0.5% calcium, 0.4% phosphorus; Madison, Wis.) and water. The animals are allowed one day to acclimate to these conditions prior to experimental manipulation.

The test compound is suspended in 20% β-cyclodextrin (CDX). 20% CDX is used as the control vehicle. 17α-Ethynyl-estradiol (obtained from Sigma Chemical Co., St. Louis, Mo.) also dissolved in 20% CDX, is used as an internal standard for these studies.

On the third day post-ovariectomy dosing with test compounds is initiated. Oral gavages of 20% CDX, Compound 1(0.1 to 10 mg/kg) or 17α-ethynyl-estradiol (100 µg/kg) are delivered daily for 35 consecutive days. On the evening following the final dose, the animals are fasted. The animals are anesthetized with a mixture of Ketaset ® and Rompun ® (67 and 6.7 mg/kg, respectively) the next morning, and a 3-mL sample of blood is obtained by cardiac puncture. The animals are then asphyxiated with carbon dioxide, and body weight and uterine weight are recorded. The left femur is removed from each animal, cleaned and frozen for subsequent x-ray evaluation.

The distal end of the femur is X-rayed using a Norland NXR-1200 X-ray machine with a voltage of 47 kV and contrast at 4.5. Digitized X-ray images are transferred directly to a Macintosh computer station, and image analysis of the X-ray scan is conducted using the Ultimage ® software program. Quantitation is achieved by measuring the total number of pixels in a standard region of interest proximal to the growth plate, over a gray scale range of zero to 60.

Experimental groups consist of 6 to 8 rats. Data for control and treated rats are compared by one way analysis of variance (ANOVA).

The compounds of formula I exhibit a positive impact on inhibition of bone loss under this assay.

We claim:

1. A method of inhibiting bone loss comprising administering to an animal in need thereof an effective amount of a compound of formula (I):

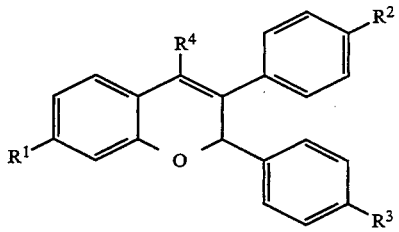

wherein:
$R^1$ and $R^2$ are, independently, —H, —OH, halo, —$OC_1$-$C_{17}$ alkyl, —$OC_3$-$C_6$ cycloalkyl, —O(CO)$C_1$-$C_{17}$ alkyl, —O(CO) aryl, —O(CO)O aryl, or —$OSO_2$-(n-butyl or n-pentyl);
$R^3$ is

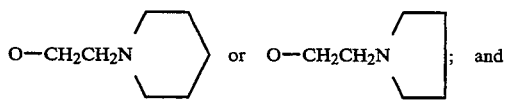

$R^4$ is —H, methyl, ethyl, propyl, ethenyl or ethynyl; or a pharmaceutically acceptable salt or solvate thereof.

2. A method according to claim 1 wherein $R^4$ is H.
3. A method according to claim 1 wherein $R^4$ is methyl, ethyl or propyl.
4. A method according to claim 3 wherein $R^4$ is methyl.
5. A method of claim 2 wherein $R^1$ and $R^2$ are each independently H, OH, or $C_{1-4}$ alkoxy.
6. A method of claim 4 wherein $R^1$ and $R^2$ are each independently H, OH, or $C_{1-4}$ alkoxy.
7. A method of claim 2 wherein $R^1$ is H.
8. A method of claim 4 wherein $R^1$ is H.
9. A method of claim 7 wherein $R^2$ is hydroxy.
10. A method of claim 8 wherein $R^2$ is hydroxy.
11. A method of claim 5 wherein $R^3$ is:

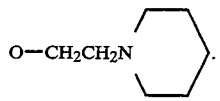

12. A method of claim 6 wherein $R^3$ is:

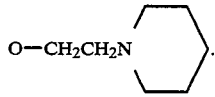

13. A method of claim 9 wherein $R^3$ is:

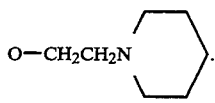

14. A method of claim 10 wherein $R^3$ is:

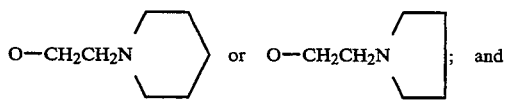

15. The method according to claim 1 wherein the said compound is 2-[4-[2-(1-piperidino) ethoxy]phenyl]-3-(4-hydroxyphenyl)-7-hydroxy-2H-1-benzopyran, 2-[4-[2-(1-piperidino)ethoxy]phenyl]-3-(4-hydroxyphenyl)-2H-1-benzopyran, 2-[4-[2-(1-piperidino)ethoxy]phenyl]-3-phenyl-7-methoxy-2H-1-benzopyran, 2-[4-[2-(1-pyrolidino)ethoxy]phenyl]-3-(4-hydroxyphenyl)-7-methoxy-2H-1-benzopyran or 2-[4-[2-(1-piperidino)ethoxy]phenyl]-3-(4-hydroxyphenyl)-4-methyl-7-hydroxy-2H-1-benzopyran.

16. A method of claim 1 wherein the animal is a human.
17. A method of claim 2 wherein the human is a female.
18. A method of claim 3 wherein the estrogen deficient.
19. A method of claim 4 wherein the female is postmenopausal.

* * * * *

UNITED STATES PATENT AND TRADEMARK OFFICE
CERTIFICATE OF CORRECTION

PATENT NO. : 5,407,947
DATED : April 18, 1995
INVENTOR(S) : Henry Bryant et al.

It is certified that error appears in the above-indentified patent and that said Letters Patent is hereby corrected as shown below:

Column 7, line 34, "aliphatic and aromatic sulfonic," should read -- aliphatic and aromatic sulfonic acids --

Column 12, line 43, "A method of claim 3 wherein the estrogen deficient." should read -- A method of claim 3 wherein the female is estrogen deficient. --

Signed and Sealed this

Sixteenth Day of July, 1996

Attest:

BRUCE LEHMAN

*Attesting Officer*   Commissioner of Patents and Trademarks